United States Patent [19]
Chiu

[11] Patent Number: 6,159,139
[45] Date of Patent: Dec. 12, 2000

[54] RADIATION DELIVERY CATHETER WITH A SPRING WIRE CENTERING MECHANISM

[75] Inventor: Jessica G. Chiu, Palo Alto, Calif.

[73] Assignee: Advanced Cardiovascular Systems Inc., Santa Clara, Calif.

[21] Appl. No.: 09/024,078

[22] Filed: Feb. 17, 1998

[51] Int. Cl.[7] .......................... A61M 25/10; A61M 29/00
[52] U.S. Cl. ............................... 600/3; 606/194; 604/104
[58] Field of Search ............................. 600/1–8; 606/194, 606/195; 604/101, 105, 106, 107

[56] References Cited

U.S. PATENT DOCUMENTS

| | | |
|---|---|---|
| 4,581,017 | 4/1986 | Sahota . |
| 4,661,094 | 4/1987 | Simpson . |
| 4,697,575 | 10/1987 | Horowitz . |
| 4,706,652 | 11/1987 | Horowitz . |
| 4,710,315 | 12/1987 | Mueller et al. . |
| 4,744,366 | 5/1988 | Jang . |
| 4,748,982 | 6/1988 | Horzewski et al. . |
| 4,762,130 | 8/1988 | Fogarty et al. . |
| 4,763,671 | 8/1988 | Goffinet . |
| 4,771,777 | 9/1988 | Horzewski et al. . |
| 4,771,778 | 9/1988 | Mar . |

(List continued on next page.)

FOREIGN PATENT DOCUMENTS

| | | |
|---|---|---|
| 0633041 | 7/1993 | European Pat. Off. . |
| 0688580 | 6/1994 | European Pat. Off. . |
| 0801961 | 4/1997 | European Pat. Off. . |
| 0829271 | 9/1997 | European Pat. Off. . |
| 0865803 | 3/1998 | European Pat. Off. . |
| 0879614 | 5/1998 | European Pat. Off. . |
| 9102312 | 2/1991 | Germany . |
| 4315002 | 5/1993 | Germany . |
| WO92/17236 | 3/1992 | WIPO . |
| WO93/04735 | 9/1992 | WIPO . |
| WO94/25106 | 5/1994 | WIPO . |

(List continued on next page.)

OTHER PUBLICATIONS

PCT Search Report PCT/US 99/03329 mailed Jun. 18, 1999.
PCT Search Report PCT/US 99/03328 mailed Jun. 18, 1999.
PCT Search Report PCT/US 99/03360 mailed Jun. 17, 1999.
Lindsay et al., "Aortic Arteriosclerosis in the Dog After Localized Aortic X–Irradiation", PP 51–60, Circulation Research, vol. X, Jan. 1962.

(List continued on next page.)

*Primary Examiner*—Samuel G. Gilbert
*Attorney, Agent, or Firm*—Blakely Sokoloff Taylor & Zafman LLP

[57] ABSTRACT

The invention is directed to a radiation delivery catheter assembly having blood perfusion capability suitable for maintaining patency of a body lumen for a period of time sufficient to allow delivery of a radiation source to the body lumen. The catheter assembly includes a spring wire centering mechanism which can be deployed between a retracted and expanded position. In the expanded position, the spring wire centering mechanism contacts a portion of the body lumen and centers a radiation source within the body lumen. In one particular embodiment, movable structural elements (spring wire legs) contact and center the adjacent portion of the catheter body within the body lumen when placed in the expanded position. In the retracted position, the spring wire mechanism is collapsed to a small profile to enable the catheter assembly to reach small diameter body lumens, such as distal coronary arteries. The spring wire centering mechanism is deployed between the retracted and expanded positions utilizing a retractable sheath which extends over the catheter body in a coaxial arrangement. This retractable sheath is movable along the length of the elongated catheter body and is designed to cover the spring wire centering mechanism to maintain it in the retracted position until the mechanism is to be deployed within the body lumen. When the retractable sheath is retracted to expose the spring wire centering mechanism, the resiliency of the spring wire legs moves the mechanism back to the expanded position.

20 Claims, 3 Drawing Sheets

U.S. PATENT DOCUMENTS

| | | |
|---|---|---|
| 4,775,371 | 10/1988 | Mueller, Jr. . |
| 4,815,449 | 3/1989 | Horowitz . |
| 4,861,520 | 8/1989 | Van't Hooft et al. . |
| 4,969,863 | 11/1990 | Van't Hooft et al. . |
| 4,976,720 | 12/1990 | Machold et al. . |
| 4,983,167 | 1/1991 | Sahota . |
| 4,994,560 | 2/1991 | Kruper, Jr. et al. . |
| 4,998,917 | 3/1991 | Gaiser et al. . |
| 5,002,560 | 3/1991 | Machold et al. . |
| 5,015,230 | 5/1991 | Martin et al. . |
| 5,019,042 | 5/1991 | Sahota . |
| 5,032,113 | 7/1991 | Burns . |
| 5,034,001 | 7/1991 | Garrison et al. . |
| 5,040,543 | 8/1991 | Badera et al. . |
| 5,046,503 | 9/1991 | Schneiderman . |
| 5,059,166 | 10/1991 | Fischell et al. . |
| 5,061,273 | 10/1991 | Yock . |
| 5,100,429 | 3/1992 | Sinofsky et al. . |
| 5,133,956 | 7/1992 | Garlich et al. . |
| 5,137,513 | 8/1992 | McInnes et al. . |
| 5,176,617 | 1/1993 | Fischell et al. . |
| 5,176,661 | 1/1993 | Evard et al. . |
| 5,180,368 | 1/1993 | Garrison . |
| 5,195,971 | 3/1993 | Sirhan . |
| 5,199,939 | 4/1993 | Dake et al. . |
| 5,213,561 | 5/1993 | Weinstein et al. ............................ 600/3 |
| 5,226,889 | 7/1993 | Sheiban . |
| 5,242,396 | 9/1993 | Evard . |
| 5,258,419 | 11/1993 | Rolando et al. . |
| 5,263,963 | 11/1993 | Garrison et al. . |
| 5,267,960 | 12/1993 | Hayman et al. . |
| 5,273,738 | 12/1993 | Matthews et al. . |
| 5,279,562 | 1/1994 | Sirhan et al. . |
| 5,282,781 | 2/1994 | Liprie . |
| 5,295,959 | 3/1994 | Gurbel et al. . |
| 5,295,960 | 3/1994 | Aliahmad et al. . |
| 5,295,995 | 3/1994 | Kleiman . |
| 5,300,281 | 4/1994 | McMillan et al. . |
| 5,302,168 | 4/1994 | Hess ............................................ 600/3 |
| 5,306,246 | 4/1994 | Sahatjian et al. . |
| 5,308,356 | 5/1994 | Blackshear, Jr. et al. . |
| 5,320,824 | 6/1994 | Brodack et al. . |
| 5,334,154 | 8/1994 | Samson et al. . |
| 5,350,361 | 9/1994 | Tsukashima et al. . |
| 5,352,199 | 10/1994 | Tower . |
| 5,354,257 | 10/1994 | Roubin et al. . |
| 5,395,333 | 3/1995 | Brill . |
| 5,405,622 | 4/1995 | Vernice et al. . |
| 5,409,495 | 4/1995 | Osborn . |
| 5,411,466 | 5/1995 | Hess . |
| 5,415,664 | 5/1995 | Pinchuk . |
| 5,441,516 | 8/1995 | Wang et al. . |
| 5,447,497 | 9/1995 | Sogard et al. . |
| 5,456,667 | 10/1995 | Ham et al. . |
| 5,458,572 | 10/1995 | Campbell et al. . |
| 5,484,384 | 1/1996 | Fearnot . |
| 5,498,227 | 3/1996 | Mawad . |
| 5,503,613 | 4/1996 | Weinberger . |
| 5,503,614 | 4/1996 | Liprie . |
| 5,507,301 | 4/1996 | Wasicek et al. . |
| 5,507,769 | 4/1996 | Marin et al. . |
| 5,516,336 | 5/1996 | McInnes et al. . |
| 5,540,659 | 7/1996 | Teirstein ...................................... 600/3 |
| 5,542,925 | 8/1996 | Orth . |
| 5,573,508 | 11/1996 | Thornton . |
| 5,573,509 | 11/1996 | Thornton . |
| 5,616,114 | 4/1997 | Thornton et al. . |
| 5,618,266 | 4/1997 | Liprie . |
| 5,653,691 | 8/1997 | Rupp et al. . |
| 5,683,345 | 11/1997 | Walksman et al. . |
| 5,688,486 | 11/1997 | Watson et al. . |
| 5,730,698 | 3/1998 | Fischell et al. . |
| 5,910,101 | 6/1999 | Andrews et al. ............................ 600/3 |
| 5,938,582 | 8/1999 | Ciamacco, Jr. et al. . |

FOREIGN PATENT DOCUMENTS

| | | |
|---|---|---|
| WO95/19807 | 1/1995 | WIPO . |
| WO96/14898 | 1/1995 | WIPO . |
| WO95/26681 | 3/1995 | WIPO . |
| WO96/06654 | 8/1995 | WIPO . |
| WO96/10436 | 9/1995 | WIPO . |
| WO96/19255 | 12/1995 | WIPO . |
| WO97/07740 | 8/1996 | WIPO . |
| WO97/37715 | 4/1997 | WIPO . |
| WO97/40889 | 4/1997 | WIPO . |
| WO98/01182 | 5/1997 | WIPO . |
| WO98/01183 | 7/1997 | WIPO . |
| WO98/01184 | 7/1997 | WIPO . |
| WO98/01185 | 7/1997 | WIPO . |
| WO98/39052 | 1/1998 | WIPO . |

OTHER PUBLICATIONS

Friedman et al., "The Antiatherogenic Effect of Iridium$^{192}$ Upon the Cholesterol–fed Rabbit", Journal of Clinical Investigation, PP 185–192 vol. 43, No. 2, Feb. 1964.

Friedman et al. "Effect of Iridium 192 Radiation on Thromboatherosclerotic Plaque in the Rabbit Aorta", PP 285–290, Archives of Pathology, vol. 80, Sep. 1965.

Hoopes et al." Intraoperative Irradiation of the Canine Abdominal Aorta and Vena Cava", International Journal Radiation Oncology Biology, Physics vol. 13, No. 5, PP 715–722, May 1987.

Weshler et al. "Inhibition by Irradiation of Smooth Muscle Cell Proliferation in the De–Endothelialized Rat Aorta", Frontiers in Radiation Biology, PP 133–138, Oct. 1988.

Dawson, "Theoretic Considerations Regarding Low–Dose Radiation Therapy for Prevention of Restenosis after Angioplasty", Texas Heart Institute Journal, vol. 18, No. 1, PP 4–7, 1991.

Johnson et al., "Review of Radiation Safety in the Cardiac Catheterization Laboratory", Radiation Safety, Catheterization and Cardiovascular Diagnosis, PP 186–194, 1992.

Schwartz et al. "Effect of External Beam Irradiation on Neointimal Hyperplasia After Experimental Coronay Artery Injury", Journal of the American College of Cardiology, vol. 19, No. 5, PP 1106–1113 Apr. 1992.

March et al., "8–Methoxypsoralen and Longwave Ultraviolet Irradiation are a Novel Antiproliferative Combination for Vascular Smooth Muscle", Circulation, vol. 87, No. 1, PP 184–191, Jan. 1993.

Katzen, "Mechanical Approaches to Restenosis in the Peripheral Circulation", Miami Vascular Institute at Baptist Hospital, Article.

Hunink et al., "Risks and Benifits of Femoropopliteal Percutaneous Balloon Angioplasty", Journal of Vascular Surgery, PP 183–194, vol. 17, No. 1, Jan. 1993.

Weintraub et al., "Can Restenosis After Coronary Angioplasty Be Predicted From Clinical Variables?", Journal of the American College of Cardiology, PP 6–14, vol. 21, No. 1, Jan. 1993.

Kuntz et al., "Generalized Model of Restenosis after Conventional Balloon Angioplasty, Stenting and Directional Atherectomy", Journal of the American College of Cardiology, vol. 21, No. 1, PP 15–25, Jan. 1993.

Haude et al., "Quantitative Analysis of Elastic Recoil after Balloon Angioplasty and after Intracoronary Implantation of Balloon–Expandable Palmaz–Schatz Stents", Journal of the American College of Cardiology, PP 26–34, vol. 21, No. 1, Jan. 1993.

Schwartz et al., "Differential Neointimal Response to Coronary Artery Injury in Pigs and Dogs", Arteriosclerosis and Thrombosis, PP 395–400, vol. 14, No. 3, Mar. 1994.

Liermann et al., "Prophylactic Endovascular Radiotherapy to Prevent Intimal Hyperplasia after Stent Implantation in Femoropopliteal Arteries", CardioVascular and Interventional Radiology, PP 12–16, 1994.

Wiedermann et al., "Effects of High–Dose Intracoronary Irradiation on Vasomotor Function and Smooth Muscle Histopathology", Intracoronary Irradiation and Vasomotion, The American Physiological Society, PP H125–H132, 1994.

Wagner et al., "Potential Biological Effects Following High X–Ray Dose Interventional Procedures", Journal of Vascular and Interventional Radiology, PP 71–84, vol. 5, No. 1, Jan.–Feb. 1994.

Wiedrmann et al., "Intracoronary Irradiation Markedly Reduces Restenosis after Balloon Angioplasty in a Porcine Model", Journal of the American College of Cardiology, PP 1491–1498, vol. 23, No. 6, May 1994.

Kakuta et al., "Differences in Compensatory Vessel Enlargement, Not Intimal Formation, Account for Restenoiss After Angioplasty in the Hupercholesterolemic Rabbit Model", Circulation, PP 2809–2815, vol. 89, No. 6, Jun. 1994.

Fischell et al., "Low–Dose –Particle Emission From 'Stent' Wire Results in Complete, Localized Inhibition of Smooth Muscle Cell Proliferation", Basic Science Reports, Circulation, PP 2956–2963, vol. 90, No. 6, Dec. 1994.

Waksman et al., "Endovascular Low–Dose Irradiation Inhibits Neointima Formation after Coronary Artery Balloon Injury in Swine", Circulation, PP 1533–1539, vol. 91, No. 5, Mar. 1, 1995.

Wiedermann et al., "Intracoronary Irradiation Markedly Reduces Neointimal Proliferation After Balloon Angioplasty in Swine: Persistent Benefit at 6–Month Follow–Up", Journal of the American College of Cardiology, PP 1451–1456, vol. 25, No. 6, May 1995.

Waksman et al., "Intracoronary Radiation Before Stent Implantation Inhibits Neointima Formation in Stented Porcine Coronary Arteries", Brief Rapid Communications, Circulation, PP 1383–1386, vol. 92, No. 6, Sep. 15, 1995.

Verin et al., "Intra–Arterial Beta Irradiation Prevents Neointimal Hyperplasia in a Hypercholesterolemic Rabbit Restenosis Model", Circulation, PP 2284–2290, vol. 92, No. 8, Oct. 15, 1995.

Waksman et al., "Intracoronary Low–Dose –Irradiation Inhibits Neointima Formation After Coronary Artery Balloon Injury in the Swine Restenosis Model", Circulation, PP 3025–3031, vol. 92, No. 10, Nov. 15, 1995.

Hehrlein et al., "Radioactive Stents", Department of Cardiology, Discoveries in Radiation for Restenosis, PP 63–64, Abstract 22, Jan. 1996.

Fischell et al., "A Beta–Particle Emitting Radioisotope Stent for the Prevention of Restenosis", Discoveries in Radiation for Restenosis, Abstract 23, PP 65, Jan. 1996.

Li et al., "A Novel Brachyehtapy Source for Treatment of Coronary Artery Restenosis" Discoveries in Radiation for Restenosis, Abstract 24, PP 67–72, Jan. 1996.

Waksman, "Catheter–Based Radiation in Stented Arteries", Discoveries in Radiation for Restenosis, Abstract 25, PP 73–74, Jan. 1996.

Martin, "Radiation For Peripheral Applications: Technical Aspects", Discoveries in Radiation for Restenosis, Abstract 27, PP 81–82, Jan. 1996.

Lumsden et al., "Restenosis In Peripheral Vascular Disease", Discoveries in Radiation for Restenosis, Abstract 28, PP 83–88, Jan. 1996.

Schopohl et al., "Endovascular Irradiation for Avoidance or Recurrent Stenosis After Stent Implantation in Peripheral Arteries–5 Year Follow–Up", Discoveries in Radiation for Restenosis, Abstract 29, PP 89–92, Jan. 1996.

Waksman, "Radiation in the Peripheral System at Emory", Discoveries in Radiation for Restenosis, Abstract 30, PP 93–94, Jan. 1996.

Teirstein, et al., "Catheter–Based Radiation Therapy to Inhibit Restenosis Following Coronary Stenting", Discoveries in Radiation for Restenosis, PP 99, Abstract 31, Jan. 1996.

King, "Clinical Restenosis Trials Using Beta Energy Radiation", Discoveries in Radiation for Restenosis, Abstract 32, PP 101–102, Jan. 1996.

Urban et al., "Endovascular Irradiation With 90Y Wire", Discoveries in Radiation for Restenosis, Abstract 33, PP 103–104, Jan. 1996.

Condado et al., "Late Follow–Up after Percutaneous Transluminal Coronary Angioplasty (PTCA) and Intracoronary Radiation Therapy (ICRT)", Discoveries in Radiation for Restenosis, Abstract 34, PP 105, Jan. 1996.

Weldon, "Catheter Based Beta Radiation System", Discoveries in Radiation for Restenosis, Abstract 35, PP 111, Jan. 1996.

Van't Hooft et al., "HDR Afterloader for Vascular Use", Discoveries in Radiation for Restenosis, PP 113, Abstract 36, Jan. 1996.

Fischell et al., "The Radioisotope Stent: Conception and Implementation", Discoveries in Radiation Restenosis, PP 115, Abstract 37, Jan. 1996.

Youri Popowski et al., "Radioactive Wire In a Self–Centering Catheter System", Discoveries in Radiation Restenosis, PP 117–118, Abstract 38, Jan. 1996.

Richard V. Calfee, "High Dose Rate Afterloader System for Endovascular Use–Neocardia", Discoveries in Radiation Restenosis, PP 119, Abstract 39, Jan. 1996.

Smith, "Issues on Handling Radioactive Devices to Prevent Restenosis", PP 121–122, Abstract 40, Jan. 1996.

Unterberg, "Reduced Acute Thrombus Formation Results in Decreased Neointimal Proliferation After Coronary Angioplasty", Journal of the American College of Cardiology, PP 1747–1754, vol. 26, No. 7, Dec. 1995.

Schwartz et al., "Effect of External Beam Irradiation on Neointimal Hyperplasia After Experimental Coronary Artery Injury", Journal of the American College of Cardiology, PP 1106–1113, vol. 19, No. 5, Apr. 1992.

Hehrlein et al., "Low Dose Radioactive Endovascular Stents Prevent Smooth Muscle Cell Proliferation and Neointimal Hyperplasia in Rabbits", Circulation, PP 1570–1575, vol. 92, No. 6, Sep. 15, 1995.

Soares et al., "Measurement of Radial Dose Distributions Around Small Beta Particle Emitters Using High Resolution Radiochromic Foil Dosimetry", Nuclear Technology Publishing, vol. 47, PP 367–372.

Byhardt, "The Heart and Blood Vessels", Radiation Oncology: Rationale, Technique, Results, PP 277–284.

PCT Search Report PCT/US 99/03327 mailed Jun. 18, 1999.

PCT Search Report PCT/US 99/03343 mailed Jun. 17, 1999.

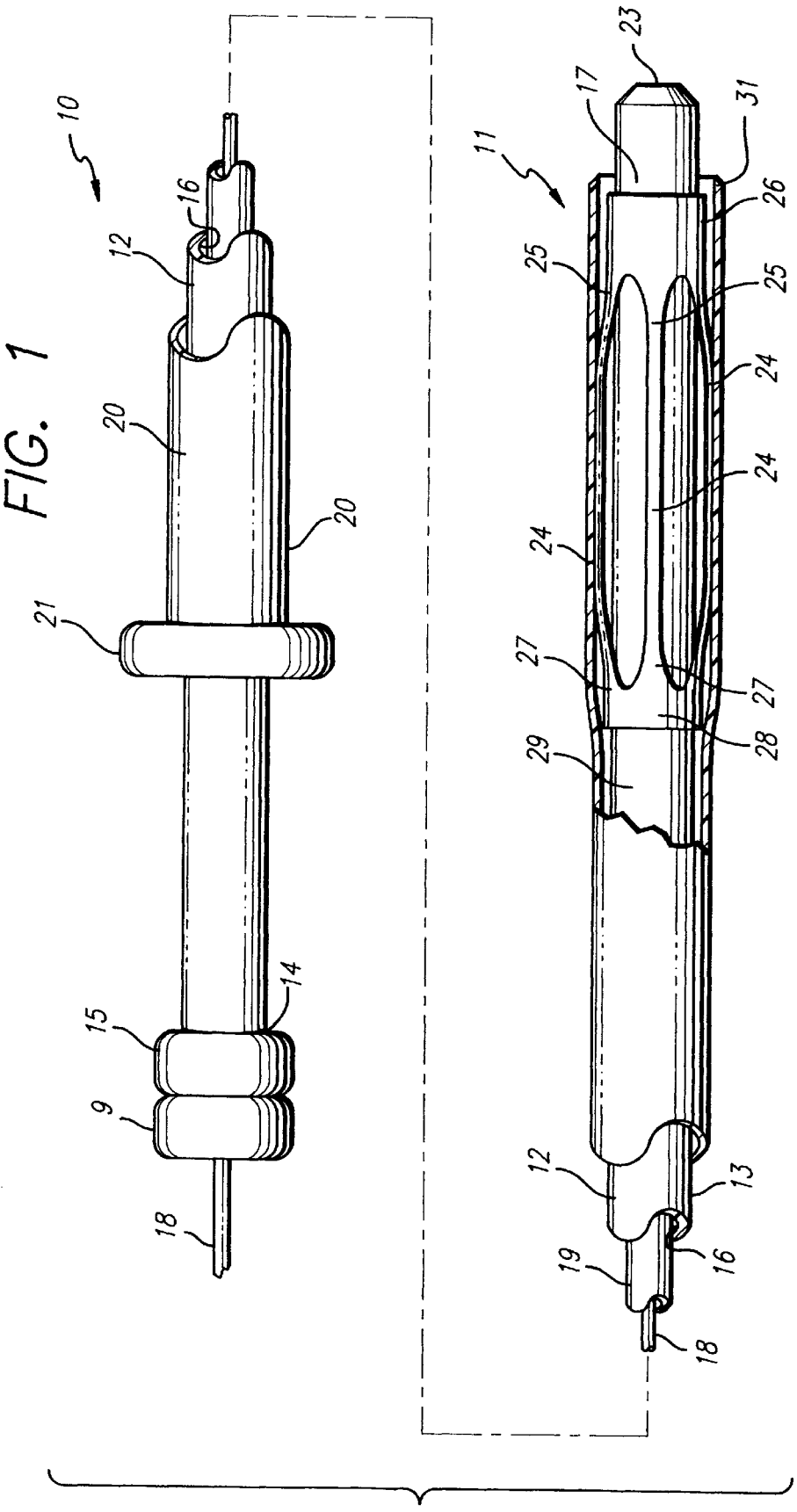

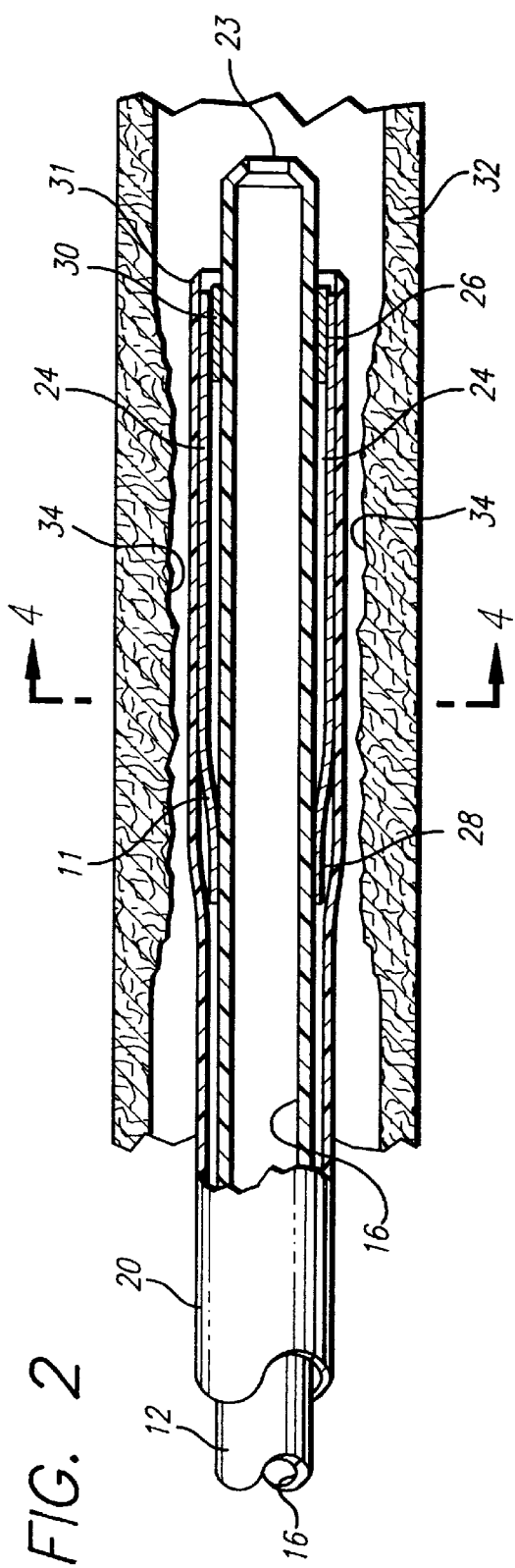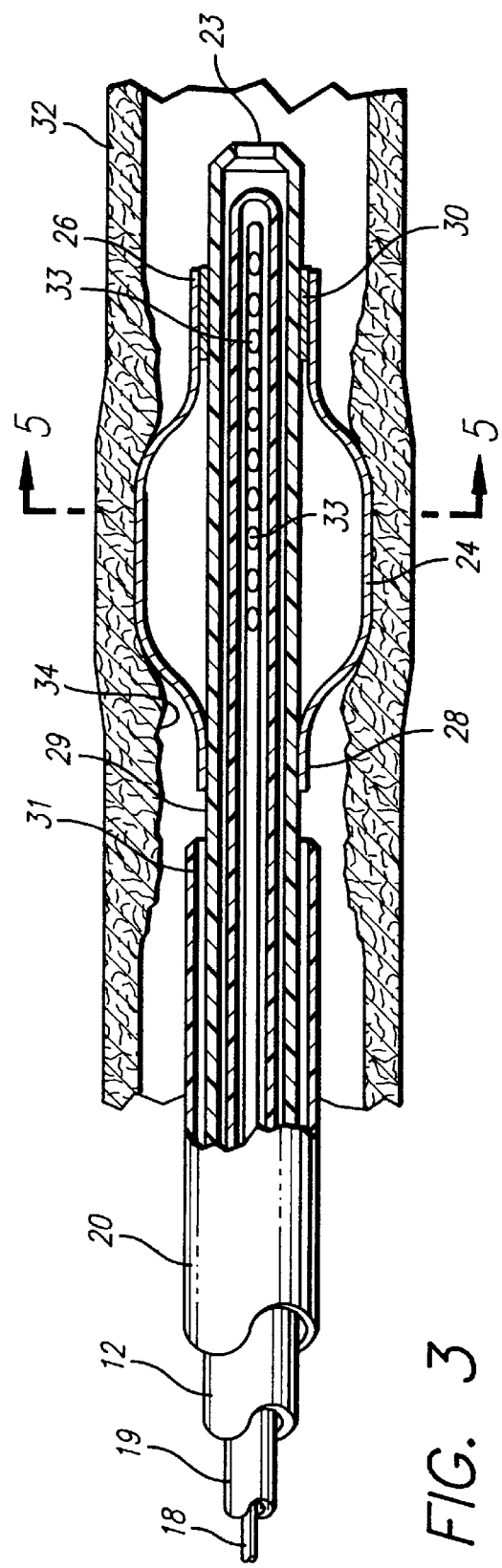

RADIATION DELIVERY CATHETER WITH A SPRING WIRE CENTERING MECHANISM

BACKGROUND OF THE INVENTION

This invention generally relates to intravascular catheters and particularly an intravascular catheter assembly having a spring wire mechanism for centering and delivering radiation treatment within a body lumen while providing blood perfusion through the body lumen past and around the catheter assembly.

In percutaneous transluminal coronary angioplasty (PTCA) procedures, a guiding catheter having a preshaped distal tip is percutaneously introduced into the cardiovascular system of a patient through the brachial or femoral artery and is advanced therein until the preshaped distal tip is disposed within the aorta adjacent to the ostium of the desired coronary artery. The guiding catheter is then twisted and torqued from its proximal end to turn its distal tip so that it can be guided into the coronary ostium. In an over-the-wire dilatation catheter system, a guide wire and a dilatation catheter having an inflatable balloon on the distal end thereof are introduced into, and advanced through, the proximal end of the guiding catheter to the distal tip of the guiding catheter seated within the coronary ostium. The distal tip of the guide wire is usually manually shaped (i.e. curved) by the physician or one of the attendants before it and the dilatation catheter are introduced into the guiding catheter. The guide wire is usually first advanced out of the distal end of the guiding catheter and is maneuvered into the patient's coronary vasculature containing the stenosis to be dilated, and is then advanced beyond the stenosis. Thereafter, the dilatation catheter is advanced over the guide wire until the dilatation balloon is positioned across the stenosis. Once the dilatation catheter is in position, the balloon of the catheter is filled with radiopaque liquid at relatively high pressures (e.g., generally about 4–12 atmospheres) to inflate it to a predetermined size (preferably the same as the inner diameter of the artery at that particular location) in order to radially compress the atherosclerotic plaque of the stenosis against the inside of the wall of the artery, thereby increasing the diameter of the occluded area. The balloon can then be deflated so that the catheter can be removed and blood flow resumed through the dilated artery.

One common problem that sometimes occurs after an angioplasty procedure has been performed is the development of restenosis at, or near, the original site of the stenosis. When restenosis occurs, a second angioplasty procedure or even bypass surgery may be required, depending upon the degree of restenosis. In order to reduce the likelihood of the development of restenosis and thereby prevent the need to perform bypass surgery or subsequent angioplasty procedures, various devices and procedures have been developed for preventing restenosis after arterial intervention. For example, an expandable cage (commonly termed "stent") designed for long term implantation with the body lumen has been utilized to help prevent the occurrence of restenosis.

More recent devices and procedures for preventing restenosis after arterial intervention employ the use of a radiation source to destroy the proliferation of smooth muscle cells which are believed to be the primary cause of restenosis. Balloon catheters have been used to deliver and maintain the radiation source in the area where arterial intervention has taken place, exposing the area to a sufficient radiation dose to abate cell growth. Two devices and methods are described in U.S. Pat. No. 5,302,168 (Hess) and U.S. Pat. No. 5,503,613 (Weinberger). Other devices and methods which utilize radiation treatment delivered by an intravascular catheter are disclosed in commonly-owned and assigned co-pending application U.S. Ser. No. 08/654,698, filed May 29, 1996, entitled Radiation-Emitting Flow-Through Temporary Stent and co-pending application Ser. No. 08/705,945, filed Aug. 29, 1996, entitled Radiation Dose Delivery Catheter with Reinforcing Mandrel, which are incorporated herein by reference. Another medical device for the treatment of a body vessel by radiation is disclosed in European Patent App. 0 688 580 A1 (Schneider).

One problem common to many of the balloon catheters which provide radiation treatment to a particular part of a patient's vascular system is that it is sometimes preferable to treat the target area with a lower radiation dosage over a longer period of time rather than a higher dosage of radiation over a shorter period of time. If conventional balloon catheters are utilized to hold open the area of an artery where restenosis is likely to occur to allow delivery of a radiation source, then the inflated balloon may inhibit or restrict the flow of blood through the artery, which can pose serious risk of damage to tissue downstream from the occluded portion of the artery since the tissue will express a deprivation of oxygenated blood. As a result, the time in which the balloon can remain expanded within the artery would be diminished, effecting the time period in which the radiation dosage can be maintained in the area of the artery where restenosis may occur. Thus, a higher dosage of radiation may have to be administered over a shorter period of time due to the occlusion of the vessel caused by the inflated balloon catheter, which again, may not be as advantageous as providing a lower dosage over a longer period of time.

What has been needed and heretofore generally unavailable in catheters which provide treatment of the body vessel with a radiation source is an intravascular catheter assembly which allows delivery of a radiation source to the area where restenosis may occur for a period of time sufficient to exhibit the cell growth and prevent development of restenosis while still allowing blood to perfuse pass the occluded region during the radiation procedure. Such a catheter assembly should be capable of centering the radiation source within the body lumen to more evenly administer the radiation to the surrounding tissue and to prevent or reduce the development of radiation burns or "hot spots" on tissue which is place too close to the radiation source. Further, such an intravascular catheter assembly should be relatively easy and inexpensive to manufacture, and capable of being formed in a variety of shapes to allow flexibility in the amount and pattern of expansion and deformation of the portion of the catheter which centers and maintains the radiation source within the body lumen. The present invention satisfies these and other needs as will be described hereinafter.

SUMMARY OF THE INVENTION

The present invention is directed to a radiation delivery catheter assembly having a spring wire centering mechanism located at the distal end of the catheter body which can be positioned and centered within a body lumen for a sufficient period of time to permit delivery of a radiation source to the body lumen while permitting perfusion of blood through the vessel.

The radiation delivery catheter assembly in accordance with the present invention includes an elongated catheter body having a proximal end and a distal end. The elongated catheter body can be made from a single tubular member having an inner radiation source lumen extending from the proximal end of the elongated catheter body to its distal portion where the radiation treatment is to be administered. A spring wire centering mechanism attached to the outer surface of the elongated catheter body near the distal end can be deployed to an expanded position to contact a portion of the body lumen and center the radiation source within the body lumen while still permitting perfusion of blood past and over the spring wire centering mechanism.

The spring wire centering mechanism normally retains a particular shape in which movable structural elements (spring wire legs) are oriented in their outwardly most extending condition (referred to as the expanded position) which causes the legs to contact and center the adjacent portion of the catheter body within the body lumen. The spring wire centering mechanism is made from a resilient material which allows the spring wire legs to be compressed to a retracted condition (referred to as the retracted position) which allows the catheter assembly and spring wire mechanism to be collapsed to a small profile to reach small diameter body lumens, such as distal coronary arteries.

The spring wire centering mechanism can be moved between the retracted and expanded positions utilizing a retractable sheath which extends over the catheter body in a coaxial arrangement. This retractable sheath is movable along the length of the elongated catheter body and is designed to cover the spring wire centering mechanism to maintain it in the retracted position until the mechanism is to be deployed within the body lumen. Once the catheter assembly is advanced to the target area of the body lumen, the retractable sheath is retracted to expose the spring wire centering mechanism, allowing the resiliency of the spring wire elements to move the mechanism back to the normally expanded position. Once the spring wire centering mechanism is deployed, the legs of the mechanism contact the wall of body lumen to center the adjacent portion of the catheter body within the body lumen. A radiation source can then be advanced through the radiation source lumen which remains centered in the target area of the body lumen. The spring wire centering mechanism can be placed in its retracted position by moving the retractable sheath over the spring wire mechanism, causing the resilient spring wire legs to collapse back to the retracted position, allowing the catheter assembly to be removed from the body lumen.

The spring wire centering mechanism is configured to be flexible so that it can be expanded on a curved portion of a body lumen, such a coronary artery. It is also configured to center a radiation source wire within the radiation source lumen, even if the spring wire centering mechanism is positioned on a curved section of the body lumen. Due to the open structure of the spring wire centering mechanism, blood is allowed to flow past the spring wire mechanism to supply oxygenated blood to tissue downstream from the catheter whenever the spring wire centering mechanism is placed in its expanded position. This open structure of the spring wire centering mechanism also causes less disturbance to distal blood flow, less contact area with the wall of the body lumen, and provides a small profile which enables the catheter assembly to reach even the most distal lesions.

In one particular embodiment of the present invention, the spring wire centering mechanism is made from a plurality of expandable spring wire legs, each having a first end which connects a first collar-like member. Likewise, each spring wire leg has a second end which connects with a second collar-like member. One of these collar-like members is securely affixed to the outer surface of the elongated catheter body while the other collar-like member remains free to move lengthwise along the elongated catheter body. This creates a free moving mechanism which is capable of sliding along the surface of the catheter body as the spring wire centering mechanism moves between the retracted and expanded positions. The spring wire legs are spaced in a staggered arrangement around the catheter body so that when placed in the expanded position, the arrangement of spring wire legs centers the adjacent catheter body within the body lumen. As a result, the radiation source will be centered in this portion of the body lumen as well. As a result of centering the radiation source within the body lumen, the radiation therapy can be administered more evenly and the possibility of developing radiation burns or "hot spots", which may form if the radiation source is placed too close to the wall of the body lumen, can be reduced or prevented.

The radiation source lumen can extend through an opening in the distal end of the elongated catheter body to allow a guide wire to be used to advance the elongated catheter body to the target area in the body lumen using well known "over-the-wire" techniques. Additionally, the spring wire centering mechanism of the present invention can be used on a single or multiple lumen radiation delivery catheter having dilating or non-dilating features.

These and other advantages of the invention will become more apparent from the foregoing detailed description thereof when taken in conjunction with the accompanying exemplary drawings.

BRIEF DESCRIPTION OF THE DRAWINGS

FIG. 1 is an elevational view, partially in cross-section, of a radiation delivery catheter assembly with a spring wire centering mechanism for centering a radiation source within a body lumen which embodies features of the present invention.

FIG. 2 is an elevational view, partially in cross-section, of the spring wire centering mechanism of the radiation delivery catheter assembly of FIG. 1, depicting the spring wire mechanism in the retracted position within a body lumen, such as an artery.

FIG. 3 is an elevational view, partially in cross-section, of the spring wire centering mechanism of the radiation delivery catheter assembly of FIG. 1, depicting the spring wire mechanism in the expanded position within a body lumen, such as an artery.

DETAILED DESCRIPTION OF THE PREFERRED EMBODIMENTS

Figure 4:
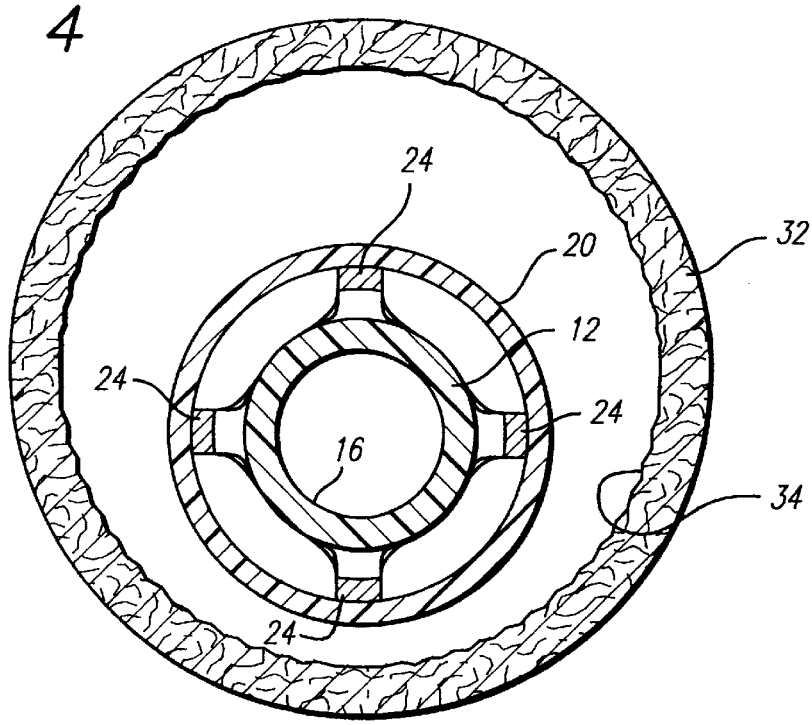
FIG. 4 is a cross-sectional view of the spring wire mechanism of FIG. 2 taken along lines 4—4.
Figure 5:
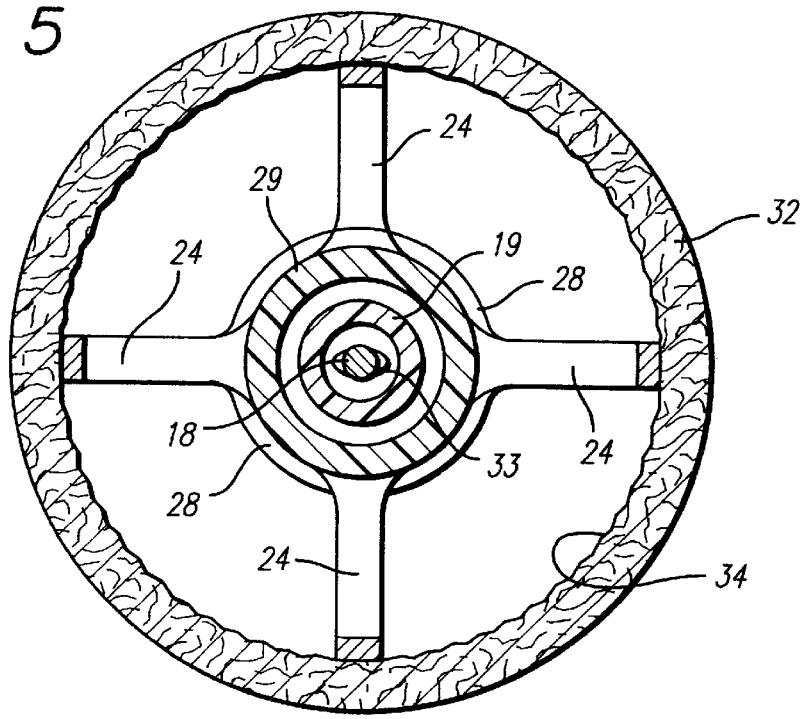
FIG. 5 is a cross-sectional view of the spring wire mechanism of FIG. 3 taken along lines 5—5.

The present invention provides a radiation delivery catheter assembly for delivering and maintaining a low dose radiation source to a patient's body lumen, such as a coronary artery or other vessel, for an extended period of time. The catheter assembly permits perfusion of blood during the radiation therapy and centers the radiation source so that equal amounts of radiation will be applied to the artery. While the invention is described in detail as applied to the coronary arteries, those skilled in the art will appreciate that it can also be used in other body lumens as well, such as peripheral arteries and veins. Where different embodiments have like elements, like reference numbers have been used.

FIGS. 1–5 illustrate a radiation delivery catheter assembly 10 with a spring wire centering mechanism 11 embodying features of the present invention. The catheter assembly 10 generally includes an elongated catheter body 12 having the spring wire centering mechanism 11 placed near the distal end thereof. In the particular embodiment shown in FIGS. 1–5, the elongated catheter body 11 is made from a single tubular member 13 having a proximal end 14 connected to luer fitting 15. A radiation source lumen 16 extends from the proximal end 14 to the distal end 17 of the catheter body 12 for receiving a radiation source wire 18. A protective sheath 19 encases the radiation source wire 18 to prevent the radiation source from being exposed to any bodily fluids, such as blood, and to provide a sterile barrier between the radiation source wire (which can be reusable and is not sterile) and the patient's vascular system. It is preferable that the radiation source wire be stored and its deployment controlled by an afterloader (not shown) which is known in the art. Second luer fitting 9 is positioned on the proximal end of catheter body 12 and is connected to the afterloader to allow the radiation source wire 18 to be placed and advanced within the radiation source lumen 16. The proximal end of protective sheath 19 is attached to the distal side of luer fitting 9 while the afterloader is attached to the proximal side of luer fitting 9.

The catheter assembly 10 includes a retractable sheath 20 which extends coaxially around the elongated catheter body 12. Another fitting 21 is located at the proximal end 22 of the retractable sheath 20 which allows the user to grasp the proximal end 22 of the retractable sheath 20 to deploy or retract the spring wire centering mechanism 11 during use.

The distal end 17 of the elongated catheter body 12 includes an opening 23 which is in communication with the radiation source lumen 16 to allow a guide wire (not shown) to be slidably disposed within the radiation source lumen 16 to facilitate the advancement and withdrawal of the catheter assembly 10 within the body lumen using well known "over-the-wire" techniques.

Alternatively, the catheter body 12 could be made utilizing a multi-lumen design, or co-axial design, which provides a separate radiation source lumen and a separate guide wire lumen without departing from the spirit and scope of the present invention. The present embodiment shows a non-dilating catheter assembly which utilizes features of the present invention. It should be appreciated that an embodiment having dilating capability also could be made utilizing features of the present invention. Such an embodiment would include a dilatation balloon or similar dilating component could be implemented in accordance with the present invention. In such an embodiment, the spring wire centering mechanism would be placed proximally to the dilatation balloon and would be deployed after arterial intervention has been performed, either by PTCA, atherectomy, stenting or other means to help abate the proliferation of smooth muscle cells in the target region. Additionally, the spring wire centering mechanism could be sized to fit an existing dilating catheter of similar interventional device to create a composite device which later can be used in administering radiation treatment.

In one particular embodiment of the present invention, the spring wire centering mechanism 11 is made with a plurality of individual spring wire legs 24 which extend lengthwise along the elongated catheter body 12. Each spring wire leg 24 has a first end 25 which is connected to a first collar-like member 26. Likewise, each spring wire leg 24 has a second end 27 which is connected to a second collar-like member 28. It should be appreciated that each spring wire leg could be made separately requiring the first and second ends 25 and 27 to be attached to the first and second collar-like members 26 and 28 utilizing any one of several techniques such as brazing, heat shrinking, heat bonding or adhesive bonding when appropriate. Alternatively, the spring wire legs 24 and collar-like members could be made from a single piece of resilient material.

Either the first or second collar-like member is securely affixed to the outer surface 29 of the elongated catheter body 12. In the embodiment described herein, the first collar-like member 26 is fastened to a gold band marker 30 which is already affixed to the outer surface 29 of the catheter body 12. The collar-like member 26 can be attached to this marker 30 using adhesive bonding, heat bonding or similar bonding techniques. The second collar-like member encircles the elongated catheter body, but remains free to move along the length of the catheter body 12 as the spring wire centering mechanism is either deployed or retracted.

It should be appreciated that the spring wire centering mechanism can be made in various sizes and structural configurations from that disclosed herein. For example, it is possible to secure both collar-like members to the catheter body and utilize spring wire legs which can be retracted and expanded without relative movement of the ends of the legs, provided the spring wire legs have sufficient elasticity to move between the retracted and expanded positions. Similarly, a centering mechanism having only a single collar-like member could be used, along with many other different combinations of similar structural elements.

In use, the spring wire centering mechanism 11 usually remains in the expanded position (FIGS. 3 and 5), but is compressible to the retracted position (FIGS. 2 and 4) to allow the catheter assembly to be advanced to distal coronary lesions where the diameter of the artery can be quite small. Due to the resiliency of the spring wire centering mechanism 11, once the retractable sheath is removed from the spring wire centering mechanism 11, the spring wire legs 24 immediately spring to the expanded position to contact the wall of the body lumen, centering the adjacent portion of the catheter within the body lumen. Thereafter, the radiation source wire 18 will be centered in that portion as well when advanced to the target area.

The spring wire centering mechanism 11 is initially placed in the retracted position by moving the distal end 31 of the retractable sheath over the spring wire centering mechanism 11. This can be accomplished by grasping the fitting 21 on the retractable sheath and simply moving it over the spring wire centering mechanism 11. A compressive force may be applied by the user's fingers to help retract the spring wire legs. Thereafter, the user can deploy the spring wire centering mechanism 11 by simply grasping the fitting 21 and moving it towards the luer fitting 15, causing the spring wire centering mechanism 11 to be exposed. Retraction of the spring wire centering mechanism 11 within the artery can be achieved by grasping the fitting 21 once again and moving it towards the distal end of the catheter body. The distal end 31 of the retractable sheath 20 should receive the second collar-like member causing the legs to snap back to the retracted position. It may be beneficial to slightly flare the distal end 31 of the retractable sheath to ensure that the opening 23 of the retractable sheath 20 will receive the second collar-like member 26 without catching.

As can be seen in FIGS. 2 and 3, once the catheter assembly 10 has been properly positioned within the body lumen, such as a coronary artery 32, the radiation source wire 18 can be inserted into the radiation source lumen 16 for a period of time sufficient to provide the radiation dosage to the lumen. Preferably, the radiation source wire 18 is hollow at its distal end and contains a radiation dose in the form of a radiation source 33, such as pellets, radiation gas, or radioactive liquid or paste. The radiation source wire 20 may also have a radioactive source coated on its distal end. This radiation source wire 18 provides the proper doses of radiation to the areas of the artery 32 where arterial intervention has been performed, either by PTCA, atherectomy, stenting or other means to help abate the proliferation of smooth muscle cells in this region.

In practice, once the catheter assembly 10 has been placed within the vasculature of the patient, the spring wire centering mechanism 11 is usually not centered within the body lumen, as shown in FIG. 4. Centering can be attained by removing the retractable sheath 20 to cause the legs of the spring wire centering mechanism 11 to snap back into the expanded position to contact the internal wall 34 of the artery 32. Again, this can be easily performed by moving the proximal end of the catheter body towards the luer fitting 15. Thereafter, the radiation source wire 18 can be advanced through the radiation source lumen 16 to the target area. Once the required period of time for radiation treatment has been completed, the spring wire centering mechanism 11 is again retracted, allowing the catheter assembly and radiation source wire to be removed from the body lumen.

It is noted that reference herein to the "target area" means that part of the body lumen that has received a PTCA, atherectomy or similar procedure to reduce or remove a stenosis, which is subject to the development of restenosis caused, in part, by intimal hyperplasia or the proliferation of smooth muscle cells.

Generally, the dimensions of the catheter assembly of the present invention are essentially the same dimensions of catheter assemblies used in angioplasty procedures. The overall length of the catheter body may be about 100 to 175 cm when a Seldinger approach through the femoral artery is employed. The diameter of the catheter body may range from about 0.030 to 0.065 inches. The spring wire centering mechanism in the retracted position has a slightly larger diameter than the catheter body, but may be expanded to a diameter of about one to about 5 mm for coronary arteries and substantially larger (e.g., 10 mm) for peripheral arteries. The diameter of the guide wire lumen should be sufficiently larger than the diameter of the guide wire to allow the catheter to be easily advanced and removed over the guide wire. Additionally, the diameter of the guide wire lumen should be sufficiently larger than the diameter of the radiation source wire and protective sleeve to allow these two devices to be easily advanced and removed from within the guide wire lumen.

The catheter body 12 includes a luer fitting which can be connected to an afterloader (not shown) to allow the radiation source to be stored away from medical personnel until the radiation therapy is to be administered to the target area. For this reason, the length of the catheter body may be much longer than the length of the retractable sheath 20 to allow the catheter body to reach the afterloader.

The particular size, shape and location of the spring wire centering mechanism 11 can be varied without departing from the spirit and scope of the present invention. For example, while each spring wire leg 24 is shown as a band-like structure, the shape of the leg could also be made cylindrical, or any other shape, provided the leg has the ability to collapse and expand between a retracted and expanded position. Such variations to the spring wire legs should achieve the same results of creating a composite arrangement of outwardly extending elements which center and maintain the radiation source within the body lumen. Additionally, the number of spring wire legs and their location relative to the catheter body can be varied without departing from the spirit and scope of the present invention.

In use, the spring wire centering mechanism 11 is maintained in its expanded position for a time sufficient to allow the radiation dosage to effect those cells which would otherwise cause restenosis to develop. Preferably, a sufficient dose of radiation can be delivered from about one minute to about sixty minutes to prevent development of restenosis. In its expanded condition, the spring wire legs press against, or at least comes in close proximity to, the internal wall 34 of the artery 32 and in doing so center the radiation source wire within the artery. Centering of this radiation source wire is important so that all portions of the artery receive as close to uniform and equal amounts of radiation as possible. Also, centering helps prevent radiation burns or hot spots from developing on portions of the target area.

The catheter assembly of the present invention as described herein is generally employed after an atherectomy, percutaneous transluminal coronary angioplasty procedure, or stent implantation to allow the radiation dose to be administered to an area where restenosis might otherwise develop within a coronary artery. It should be recognized by those skilled in the art that the catheter of the present invention can be used within a patient's vasculature system after vascular procedures other than a PTCA, stent implantation or atherectomy have been performed.

The catheter assembly of the present invention may be formed from conventional materials of construction which are described in detail in prior art patents referenced herein. The materials forming the catheter body, protective sheath and retractable sheath can be made out of relatively inelastic materials, such as polyethylene, polyvinyl chloride, polyesters and composite materials.

The various components may be joined by suitable adhesives such as the acrylonitrile based adhesive sold as Loctite 405. Heat shrinking or heat bonding may also be employed when appropriate. The spring wire centering mechanism 11 can be made from such materials as stainless steel, nickel-titanium alloys, Nylon, aramid, or other suitable resilient materials. The radiation source wire can be made from materials such as stainless steel, titanium, nickel-titanium and platinum-nickel alloys, or any NiTi alloys, or any polymers and composites. It should be appreciated that variations can be made in the composition of the materials to vary properties.

As described herein, the catheter assembly will deliver a low dosage of radiation through the body lumen, such as a coronary artery, and is configured to provide the dosage over longer periods of time if necessary, due to the catheter's ability to allow blood to perfuse past the inflatable region during treatment. It is preferred that a low dosage of radiation, on the order of about 0.1 up to about 3.0 curies be the typical radiation dose provided to treat, for example, a coronary artery. Preferably, 1 to 2 curies will provide a proper dosage level.

The radiation delivered to a coronary artery should be in the range from about 20 to 3,000 rads in preferably not less than thirty seconds. The radiation dose can be delivered in less than thirty seconds, however, it is preferable that a longer time frame be used so that a lower dose can be administered in the target area.

It is contemplated that different radiation sources be used, and the preferred radiation sources include iridium$^{192}$ if alpha radiation is used, and phosphorus$^{32}$ if beta particles are used. Further, it is contemplated that the radiation sources may provide beta particles or gamma rays to affect the target cells. However, alpha emitting radiation sources also can be used even though such radiation does not travel very far in human tissue. The use of beta and gamma emitting radiation sources is well known for treating and killing cancerous cells.

Other modifications can be made to the present invention without departing from the spirit and scope thereof. The specific dimensions, doses, times and materials of constructions are provided as examples and substitutes are readily contemplated which do not depart from the invention.

What is claimed is:

1. A radiation centering catheter assembly for maintaining the patency of a body lumen for a period of time sufficient to permit delivery of a radiation dose to the body lumen while permitting blood perfusion, comprising:

an elongated catheter body having a proximal end and a distal end;

a radiation source lumen extending through at least a portion of the elongated catheter body for receiving a radiation source to provide a radiation dose to the body lumen;

a spring wire centering mechanism located near the distal end of the elongated catheter body, the spring wire centering mechanism including a plurality of spring wire legs coupled to at least one collar-like member disposed around the elongated catheter body the spring wire centering mechanism being movable between a retracted position and an expanded position such that when in the expanded position, the mechanism contacts a portion of the body lumen and centers at least the adjacent portion of the catheter body within the body lumen while permitting perfusion of blood past and over the spring wire centering mechanism; and a retractable sheath extending coaxially over the elongated catheter body and being movable in the lengthwise direction along the elongated catheter body, the retractable sheath being movable to cover the spring wire centering mechanism to place the mechanism in the retracted position and to uncover the mechanism to deploy the mechanism into the expanded position.

2. The catheter assembly of claim 1, wherein the plurality of spring wire legs are made from a resilient material, the plurality of spring wire legs collapsing when the spring wire centering mechanism is placed in the retracted position and expanding outward away from the elongated catheter body when placed in the expanded position.

3. The catheter assembly of claim 1, wherein each spring wire leg has a first end and a second end, each of the first ends being connected with a first collar-like member and each of the second ends being connected to a second collar-like member, the first and second collar-like members being disposed around the elongated catheter body.

4. The catheter assembly of claim 3, wherein one of the first or second collar-like members is securely affixed to the outer surface of the elongated catheter body with the other collar-like member being free to move lengthwise along the elongated catheter body as the spring wire centering mechanism is moved between the retracted and expanded positions.

5. The catheter assembly of claim 1, further including a protective sheath adapted to encase a radiation source, the protective sheath being insertable within the radiation source lumen to provide a barrier between a radiation source and the body lumen.

6. The catheter assembly of claim 1, further including a dilatation balloon disposed near the distal end of the elongated catheter body and means for inflating and deflating the dilatation balloon.

7. The catheter assembly of claim 6, wherein the spring wire centering mechanism is placed proximal to the dilatation balloon.

8. The catheter assembly of claim 1, further including a guide wire lumen extending through at least a portion of the elongated catheter body for receiving a guide wire used to advance the elongated catheter body to the area in the body lumen where the radiation dose is to be delivered.

9. The catheter assembly of claim 1, wherein the radiation source lumen extends through an opening at the proximal end of the catheter body and is adapted for receiving a guide wire used to advance the elongated catheter body to the area in the body lumen where the radiation dose is to be delivered.

10. A method for maintaining the patency of a body lumen for a period of time sufficient to permit delivery of a radiation dose to the body lumen while permitting blood perfusion, comprising the steps of:

a) providing a catheter having:

an elongated catheter body having a proximal end and a distal end;

a radiation source lumen extending through at least a portion of the elongated catheter body for receiving a radiation source to provide a radiation dose to the body lumen;

a spring wire centering mechanism located near the distal end of the elongated catheter body, the spring wire centering mechanism including a plurality of spring wire legs coupled to at least one collar-like member disposed around the elongated catheter body, the spring wire centering mechanism being movable between a retracted position and an expanded position such that when in the expanded position, the mechanism contacts a portion of the body lumen and centers at least the adjacent portion of the catheter body within the body lumen while permitting perfusion of blood past and over the spring wire centering mechanism; and a retractable sheath extending coaxially over the elongated catheter body and being movable in the lengthwise direction along the elongated catheter body, the retractable sheath being movable to cover the spring wire centering mechanism to place the mechanism in the retracted position and to uncover the mechanism to deploy the mechanism into the expanded position;

b) placing the spring wire centering mechanism in the retracted position on the elongated catheter body;

c) advancing the catheter assembly until the spring wire centering mechanism is in proper position in the body lumen;

d) retracting the retractable sheath to deploy the spring wire centering mechanism in the expanded position to contact and center the adjacent portion of the catheter body within the body lumen;

e) inserting a radiation source into the radiation source lumen and advancing the radiation source to the portion of the catheter body which has been centered within the body lumen to administer the radiation dose;

f) placing the spring wire centering mechanism in the retracted position; and g) withdrawing the catheter assembly and the radiation source from the body lumen.

11. A radiation centering catheter comprising:

an elongated catheter body having a proximal end and a distal end;

a radiation source lumen extending through at least a portion of the elongated catheter body for receiving a radiation source to provide a radiation dose to a body lumen;

a plurality of spring wire centering legs coupled to at least one collar-like member disposed around the elongated catheter body; and a retractable sheath extending coaxially over the elongated catheter body and being movable in the lengthwise direction along the elongated catheter body to cover the spring wire centering legs to place the spring wire centering legs in a retracted position and to uncover the spring wire centering legs to deploy the spring wire centering legs into an expanded position.

12. The catheter assembly of claim 11, wherein the plurality of spring wire legs are made from a resilient material, the plurality of spring wire legs collapsing when the spring wire centering legs are placed in the retracted position and expanding outward away from the elongated catheter body when placed in the expanded position.

13. The catheter assembly of claim 11, further including a guide wire lumen extending through at least a portion of the elongated catheter body for receiving a guide wire used to advance the elongated catheter body to the area in the body lumen where the radiation dose is to be delivered.

14. The catheter assembly of claim 11, wherein the radiation source lumen extends through an opening at the proximal end of the catheter body and is adapted for receiving a guide wire used to advance the elongated catheter body to the area in the body lumen where the radiation dose is to be delivered.

15. The catheter assembly of claim 11, further including a protective sheath adapted to encase a radiation source, the protective sheath being insertable within the radiation source lumen to provide a barrier between a radiation source and the body lumen.

16. The catheter assembly of claim 11, further including a dilatation balloon disposed near the distal end of the elongated catheter body and means for inflating and deflating the dilatation balloon.

17. The catheter assembly of claim 16, wherein the spring wire centering legs are placed proximal to the dilatation balloon.

18. The catheter assembly of claim 11, wherein each spring wire leg has a first end and a second end, each of the first ends being connected with a first collar-like member and each of the second ends being connected to a second collar-like member, the first and second collar-like members being disposed around the elongated catheter body.

19. The catheter assembly of claim 18, wherein one of the first or second collar-like members is securely affixed to the outer surface of the elongated catheter body with the other collar-like member being free to move lengthwise along the elongated catheter body as the spring wire centering legs are moved between the retracted and expanded positions.

20. A method comprising:

a) providing a catheter having:
   an elongated catheter body having a proximal end and a distal end;
   a radiation source lumen extending through at least a portion of the elongated catheter body receiving a radiation source wire to provide a radiation source to the body lumen;
   a plurality of spring wire centering legs coupled to at least one collar-like member disposed around the elongated catheter body; and
   a retractable sheath extending coaxially over the elongated catheter body and being movable in the lengthwise direction along the elongated catheter body to cover the spring wire centering legs to place the spring wire centering legs in a retracted position and to uncover the spring wire centering legs to deploy the spring wire centering legs into an expanded position;

b) placing the spring wire centering legs in the retracted position on the elongated catheter body;

c) advancing the catheter assembly until the spring wire centering legs are in proper position in the body lumen;

d) retracting the retractable sheath to deploy the spring wire centering legs in the expanded position to contact and center the adjacent portion of the catheter body within the body lumen;

e) inserting a radiation source into the radiation source lumen and advancing the radiation source to the portion of the catheter body which has been centered within the body lumen to administer the radiation dose;

f) placing the spring wire centering legs in the retracted position; and g) withdrawing the catheter assembly and the radiation source from the body lumen.

* * * * *

UNITED STATES PATENT AND TRADEMARK OFFICE
CERTIFICATE OF CORRECTION

PATENT NO.   : 6,159,139
DATED        : December 12, 2000
INVENTOR(S)  : Chiu

It is certified that error appears in the above-identified patent and that said Letters Patent is hereby corrected as shown below:

<u>Column 1,</u>
Line 7, after "particularly" insert -- to --.

<u>Column 4,</u>
Line 13, delete "bums" and insert -- burns --.

<u>Column 5,</u>
Line 51, after "been" delete -- . --.

Signed and Sealed this

Twenty-sixth Day of February, 2002

*Attest:*

JAMES E. ROGAN
*Attesting Officer*           *Director of the United States Patent and Trademark Office*